Oct. 24, 1944. W. E. LAMMERTS Plant Pat. 646
ROSE PLANT
Filed Feb. 5, 1944
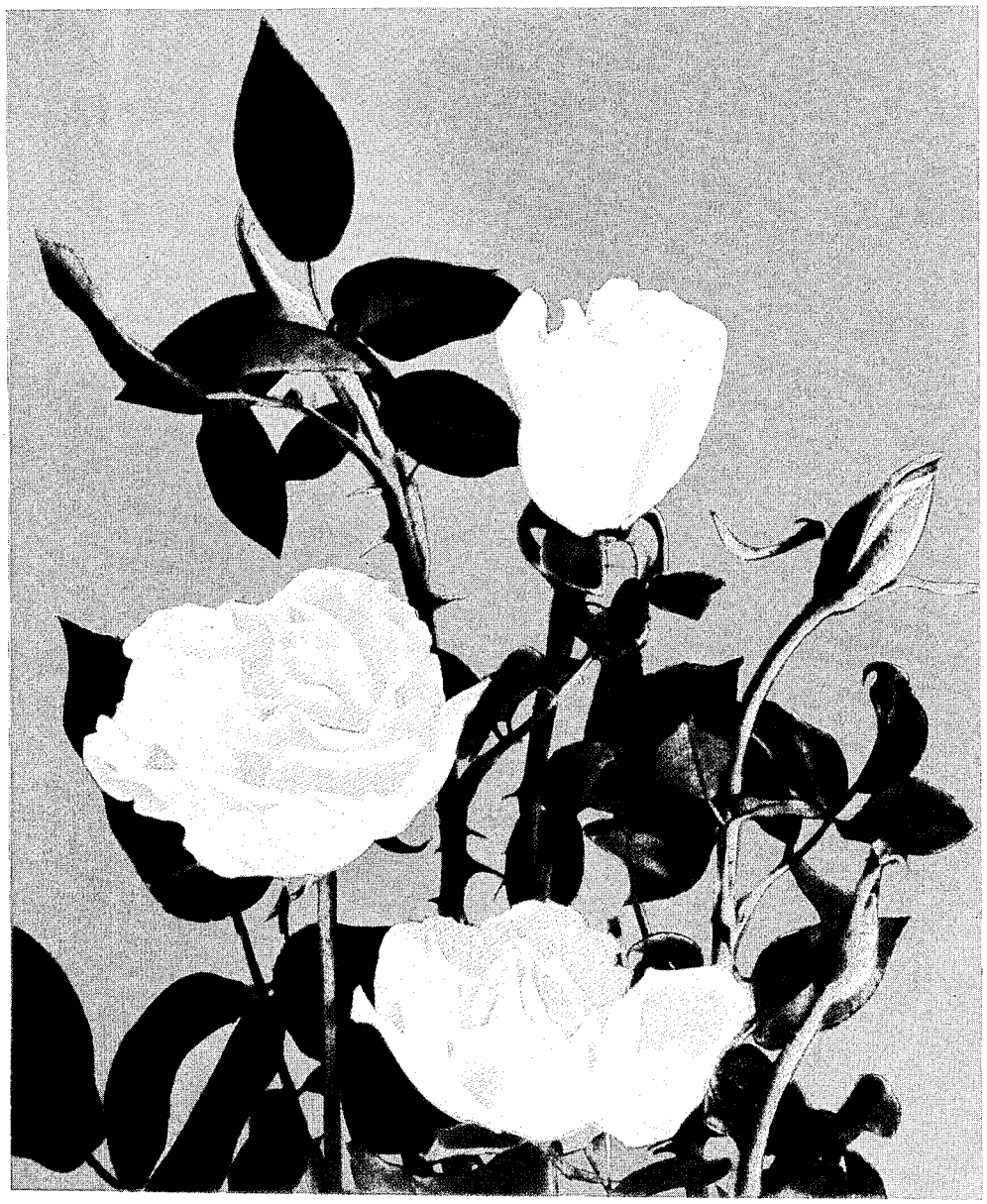
Inventor
W. E. Lammerts
By Robbins & Robbins
attorneys Patented Oct. 24, 1944

Plant Pat. 646

UNITED STATES PATENT OFFICE

646

ROSE PLANT

Walter E. Lammerts, West Los Angeles, Calif., assignor to Armstrong Nurseries, Inc., Ontario, Calif., a corporation of California Application February 5, 1944, Serial No. 521,243

1 Claim. (Cl. 47—61)

This invention relates to a new and distinct variety of rose plant, resulting from the growing of seed from a cross of the two varieties "Joanna Hill" and "Crimson Glory."

It will be noted as this description proceeds that the novelty of this new variey arises from a combination of valuable characteristics which have not heretofore been found in a hybrid tea rose, and therefore represent a very desirable improvement in hybrid teas.

Particularizing with reference to the above, the new variety is characterized principally by its extremely large, long-pointed buds produced on a tall, upright plant, with single and at times several flowers to the stem, the buds sometimes attaining a length as much as three inches and being of the type of that well known variety "Charlotte Armstrong."

Specifically, this new rose has broad, leathery, dull leaves, resistant to mildew, and the open blooms, which are usually cup-shaped and of moderate tea fragrance, have from fifteen to twenty-two petals, with from three to five petaloids arranged irregularly.

The bloom ranges in size from medium to large, usually measuring from three-and-one-half to four-and-one-half inches in diameter, and is of that shade of color popularly known as deep pink, which, technically, ranges principally from near Phlox Pink to near Rose Madder in the months of August and September in Southern California. The flowers earlier in the season are somewhat lighter in hue.

The plants vary in height from two-and-one-half to four feet where grown in the garden, depending on the fertility of the soil.

Asexual reproduction of this new variety shows the foregoing characteristics come true to form and are established.

The distinctiveness and novelty of this new variety may be recognized from the foregoing summary and are more particularly pointed out in the following detailed description in which color terminology accords with that of the Robert F. Wilson Horticultural Colour Charts:

Type: Fairly tall bush; outdoor; seedling; for cut flowers and garden decoration.

Class: Hybrid tea.

Breeding: Seedling.

*Seed parent.*—"Joanna Hill."

*Pollen parent.*—"Crimson Glory."

Propagation: Holds its distinguishing characteristics through succeeding propagations by budding, which is the only method tried up to the present.

*Flower*

Locality where grown: Ontario, California.

Flowers borne: Singly and at times several to stem; in irregular cluster; on normally strong, medium long stems.

Quantity of bloom: Free; outdoors.

Continuity: Continuous during growing season.

Fragrance: Moderate; tea.

Bud:

*Pedicel.*—Medium length; medium heavy; erect; medium rough; few gland-tipped cilia. On some pedicels are a few hairs. *Color*—near Fern Green, Plate 0862/1, page 186, Chart II.

*Before calyx breaks.*—*Size*—small to medium because sepals unfold and expose the bud at a very early stage in its development when yet quite small. *Form*—short, pointed, without a conspicuous neck; usually without foliaceous appendages, tomentum, gland-tipped cilia on the surface of the bud; with slender, much cut, bristle-like foliaceous parts extending beyond the tip of the bud equal to one-fourth or more of its length.

*As calyx breaks.*—*Color*—near Rose Madder, Plate 23, page 23, Chart I. Inner surface—with fine, woolly tomentum, on margins of alternate sepals, lined with gland-tipped cilia, stipitate and sessile glands.

*As first petal opens.*—*Size*—medium. (Petal does not fold back to any extent until the bud has reached maturity though petals all loosen considerably from the initial tightly clasping state.) *Form*—short; ovoid to globular. *Color*—Outside—near Crimson, Plate 22, page 22, Chart I. Inside—near Crimson, Plate 22, page 22, Chart I, and gradually fusing into near Crimson, Plate 22/2, page 22, Chart I. *Opening*—opens up well; relatively rapidly when bud has reached maximum size, that is, when it is very large.

Bloom:

*Size.*—When fully open—medium to large; approximately 3½ inches to 4½ inches.

*Petalage.*—Semi-double (2 or even three rows); from 15 to 22 petals; arranged regularly. 3 to 5 petaloids arranged irregularly.

*Form.*—Cupped to high center at first; becoming open to cupped; petals at first tightly flat; becoming later, at maturity, loosely flat to cupped or rolled outward.

Petals: Thick; with inside satiny and outside shiny.

*Shape.*—Outside—obovate, mucronate; sometimes scalloped apex with one or two notches occasionally. The center row of petals on some blooms are more scalloped than others. Intermediate—obovate, mucronate; scalloped at times with one or two notches. Inside—obovate, mucronate; seldom irregular apex. On the petaloids of some blooms is a distinct ridge running from base to apex, off center, and often a lighter shade.

*Color.*—Colors may be modified by being penciled and shaded with other colors.

This description of a newly opened flower was made from a rose grown outdoors and allowed to open three days indoors, in August, 1943, at Ontario, California. The description of these petals was made from a rose grown in sandy soil:

*Color.*—*Outside petal*—outside surface—near Phlox Pink, Plate 625, page 77, Chart I, toward apex near Phlox Pink, Plate 625/1, page 77, Chart I. Inside surface—near Phlox Pink, Plate 625, then to edge near apex Phlox Pink, Plate 625/1, page 77, Chart I. At base of petal, near Aureolin, Plate 3/2, page 3, Chart I. *Intermediate petal*—outside surface—this row of petals usually an even tone of near Phlox Pink, Plate 625, page 77, Chart I, on the outside and inside surfaces at base of petal near Aureolin, Plate 3/2, page 3, Chart I. *Inner petal*—outside surface—near Rose Madder, Plate 23/1, page 23, Chart I. Inside surface—near Rose Madder, Plate 23, page 23, Chart I, with more near Aureolin, Plate 3/2, page 3, Chart I, showing at base.

This description was made from a rose that was open for three days outdoors, in August, 1943, at Ontario, California. Made from a rose grown outdoors in a sandy soil. The temperature and humidity during the four days were: 86°, 37; 86°, 42; 88°, 41.

*Color.*—*Outside petal*—outside surface—near Phlox Pink, Plate 625/1, page 77, Chart I, to near Phlox Pink, Plate 625/2, towards apex, page 77, Chart I. Penciling is quite pronounced on nearly all petals. Outdoors they become yellowish white about ¼″ to ¾″ from base when blooms are almost finished. Inside surface—very little difference from outside surface, except occasionally due to more exposure to sun the color may be a trifle lighter. *Inside petal*—outside surface—even hue of near Phlox Pink, Plate 625/1, page 77, Chart I. Inside surface—similar to outside surface with a very narrow margin at top of petal of near Phlox Pink, Plate 625/3, page 77, Chart I.

*General color effect.*—Newly opened flower—all petals showing about an even tone in coloring—near Phlox Pink, Plate 625, page 77, Chart I. Three days open—near Phlox Pink, Plate 625/1, page 77, Chart I.

*Behavior.*—Drop off cleanly. Sometimes a few petaloids will cling to receptacle. When checked, flowers and color not materially affected by hot, dry weather, except some diminished size.

*Flower longevity.*—On bush in garden three to four days in August; cut roses grown outdoors kept at living room temperatures, three days in August.

*Reproductive organs*

Stamens: Medium number; arranged regularly about pistils, mixed with petaloids sometimes.

Filaments: Medium to long; most with anthers.

Anthers: Medium size; open at various times. Color, near Orpiment Orange, Plate 10/2, page 10, Chart I, to near Jasper Red, Plate 018, page 107, Chart II.

Pollen: Sparse. Color, near Chinese Yellow, Plate 606, page 68, Chart I.

Pistils: Medium to many.

Styles: Even; medium length; medium heavy; bunched.

Stigma: Color, near Chrysanthemum Crimson, Plate 824/2, Page 169, Chart II.

Ovaries: Some protruding from calyx.

Hips: Short; globular with inconspicuous neck. Color, near Citron Green, Plate 763/2, page 100, Chart I, and blotched with near Indian Lake, Plate 826/2, page 170, Chart II; hips seldom formed on the plants.

Sepals: Permanent; moderately short; recurved. Color—inside—near Erythrite Red, Plate 0027/1, page 190, Chart II. Outside—near Scheel's Green, Plate 860, page 175, Chart II.

Seeds: Few, medium size.

*Plant*

Foliage:

*Leaves.*—Compound of three to five leaflets; normally abundant; medium to large; moderately heavy; leathery.

*Leaflets.*—Shape—ovate, with apex slightly obtuse. Base—obtuse. Margin—serrate.

*Color.*—*Mature*—upper surface—from near Spinach Green, Plate 0960, page 187, Chart II, to near Parsley Green, Plate 00962, page 193, Chart II. Under surface—from near Willow Green, Plate 000862, page 199, Chart II. *Young*—upper surface—near Spinach Green, Plate 0960/3, page 187, Chart II. Under surface—near Purple Madder, Plate 1028, page 181, Chart II.

*Rachis (the supporting stem of the compound leaf).*—Medium heavy. Upper side—grooved; glandular. Under side—smooth.

*Stipules.*—Short; medium width; medium points turning out at an angle of more than 45°.

*Disease.*—Resistant to mildew.

Growth:

*Habit.*—Bushy; upright; much branched.

*Growth.*—Vigorous.

*Canes.*—Medium heavy.

*Main stems.*—Near Spinach Green, Plate 0960/2, page 187, Chart II. *Large prickles*—several; medium length; hooked downward with short, narrow base. Color—near Ochraceous Tawny, Plate XV, line i, Ridgway's color standards. *Small prickles*—few. Color—near Raw Sienna, Plate III, line i, Ridgway's color standards. *Hairs*—none.

*Branches.*—*Color*—from near Fern Green, Plate 0862, page 186, Chart II, to near Spinach Green, Plate 0960/2, page 187, Chart II. *Large prickles*—few; medium length; hooked downward; with short, narrow base. Color—near Spinel Red, Plate XXVI, Ridgway's color standards. *Small prickles*—few. *Hairs*—none.

*New shoots.—Color*—near Purple Madder, Plate 1028, page 181, Chart II. *Large prickles*—very few; medium length; some hooked downward; with short, narrow base. Color—near Purple Madder, Plate 1028, page 181, Chart II. *Small prickles*—few. *Hairs*—none.

I claim:

A new and distinct variety of rose plant characterized as to novelty by its habits of growth, color and fragrance of the flower, size and shape of the bud and open bloom, and form, texture and resistance to mildew of the plant foliage, substantially as shown and described

WALTER E. LAMMERTS.